(12) United States Patent
Spendlove et al.

(10) Patent No.: US 10,092,740 B2
(45) Date of Patent: Oct. 9, 2018

(54) SKIN PUNCTURING DEVICE

(71) Applicant: MEDMETICS, LLC, Heber City, UT (US)

(72) Inventors: Jared Spendlove, South Weber, UT (US); Tim Nieman, North Salt Lake, UT (US); Michael Anderer, Tampa, FL (US); Michael Morgan, Salt Lake City, UT (US); Jeremy Jones, Midvale, UT (US); Chad Milton, Salt Lake City, UT (US)

(73) Assignee: Medmetics, LLC, Heber City, UT (US)

( * ) Notice: Subject to any disclaimer, the term of this patent is extended or adjusted under 35 U.S.C. 154(b) by 9 days.

(21) Appl. No.: 14/496,064

(22) Filed: Sep. 25, 2014

(65) Prior Publication Data
US 2015/0151098 A1   Jun. 4, 2015

Related U.S. Application Data

(60) Provisional application No. 61/911,530, filed on Dec. 4, 2013, provisional application No. 61/938,720, filed on Feb. 12, 2014.

(51) Int. Cl.
*A61B 17/34* (2006.01)
*A61M 37/00* (2006.01)

(52) U.S. Cl.
CPC ........ *A61M 37/0076* (2013.01); *A61M 37/00* (2013.01); *A61M 2037/0046* (2013.01)

(58) Field of Classification Search
CPC ............ A61B 5/1411; A61B 5/150412; A61B 5/15117; A61B 5/15142; A61M 2037/0046; A61M 37/00; A61M 37/0076
See application file for complete search history.

(56) References Cited

U.S. PATENT DOCUMENTS

| 4,159,659 | A | | 7/1979 | Nightingale |
| 5,366,470 | A | * | 11/1994 | Ramel ................. A61B 5/1411 604/157 |
| 5,776,106 | A | * | 7/1998 | Matyas ................. A61M 25/02 128/DIG. 26 |

(Continued)

FOREIGN PATENT DOCUMENTS

| EP | 2011539 | 5/2008 |
| EP | 2420465 | 2/2012 |
| WO | WO2012140643 | 10/2012 |

*Primary Examiner* — Julie A Szpira
(74) *Attorney, Agent, or Firm* — Law Office of Scott C Harris, Inc.

(57) ABSTRACT

A safety needle assembly for skin puncturing. A plurality of needles driven by a reciprocating drive shaft extend and retract through an opening in one end of the assembly. Eleven or twelve needles are configured so as to minimize potential surface tension and reduce stress applied to the skin. The opening may be rounded or scalloped to reduce friction on the skin. An elastomeric or mechanical spring is used to assist in retracting the needles. Various alignment tabs and features are used to ensure proper alignment of the drive shaft within the assembly, and alignment of the needle assembly when attached to a handpiece during use. Safety tabs on the needle assembly prevent reuse. A protective sleeve may be used to cover the exterior of the needle assembly.

17 Claims, 22 Drawing Sheets

(56) References Cited

U.S. PATENT DOCUMENTS

| | | | | |
|---|---|---|---|---|
| 6,136,013 | A  * | 10/2000 | Marshall | A61B 5/1411 |
| | | | | 606/167 |
| 2004/0116953 | A1 | 6/2004 | Dixon | |
| 2005/0234487 | A1* | 10/2005 | Shi | A61B 5/1411 |
| | | | | 606/181 |
| 2006/0058828 | A1* | 3/2006 | Shi | A61B 5/1411 |
| | | | | 606/181 |
| 2007/0156095 | A1* | 7/2007 | Hazut | A61B 17/205 |
| | | | | 604/173 |
| 2008/0221548 | A1* | 9/2008 | Danenberg | A61Q 19/02 |
| | | | | 604/506 |
| 2010/0023003 | A1 | 1/2010 | Mulholland | |
| 2010/0330589 | A1* | 12/2010 | Bahrami | A61M 5/1452 |
| | | | | 435/7.9 |
| 2014/0094742 | A1* | 4/2014 | Won | A61M 37/00 |
| | | | | 604/46 |

* cited by examiner

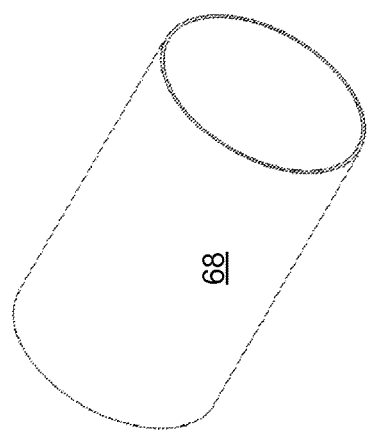
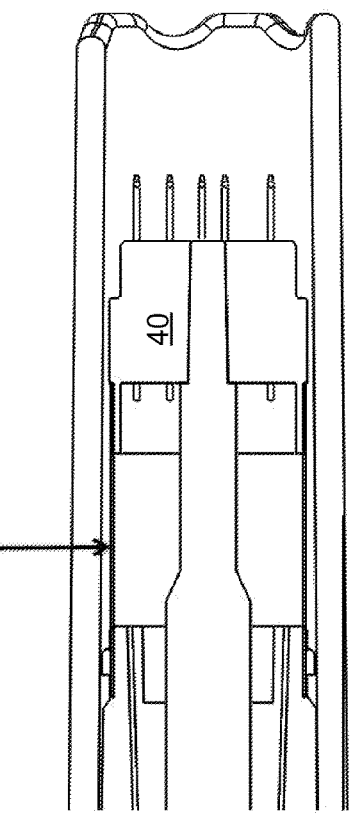
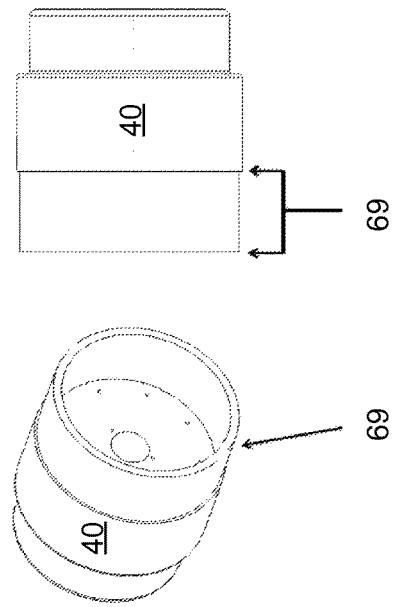
FIG. 8D
FIG. 8E
FIG. 8C

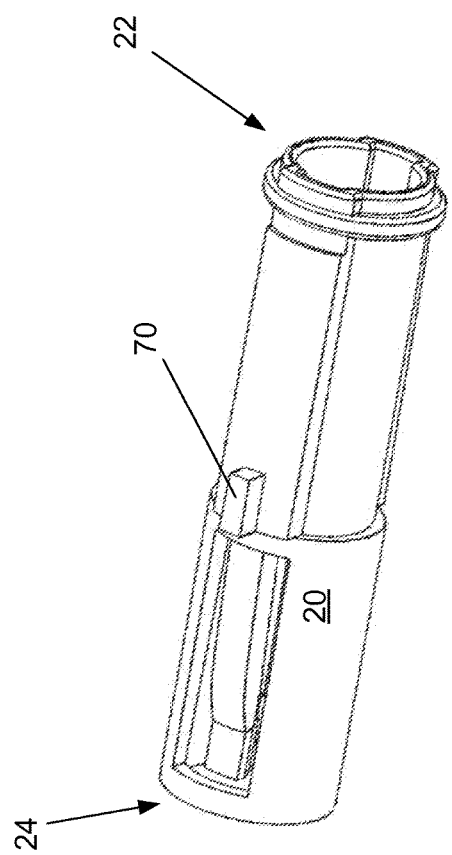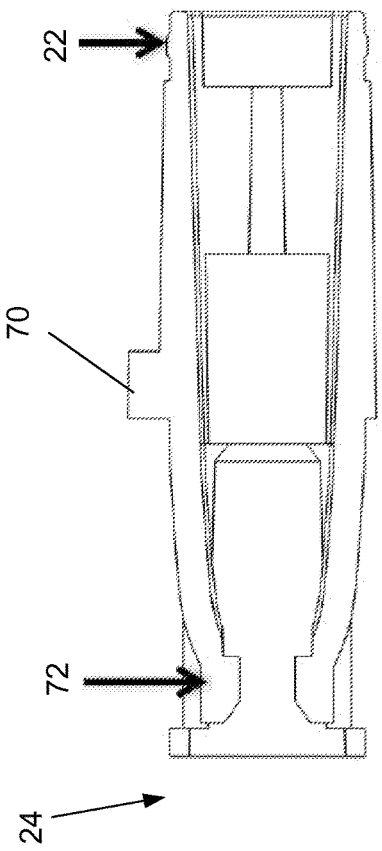
FIG. 9A
Section View
FIG. 9B

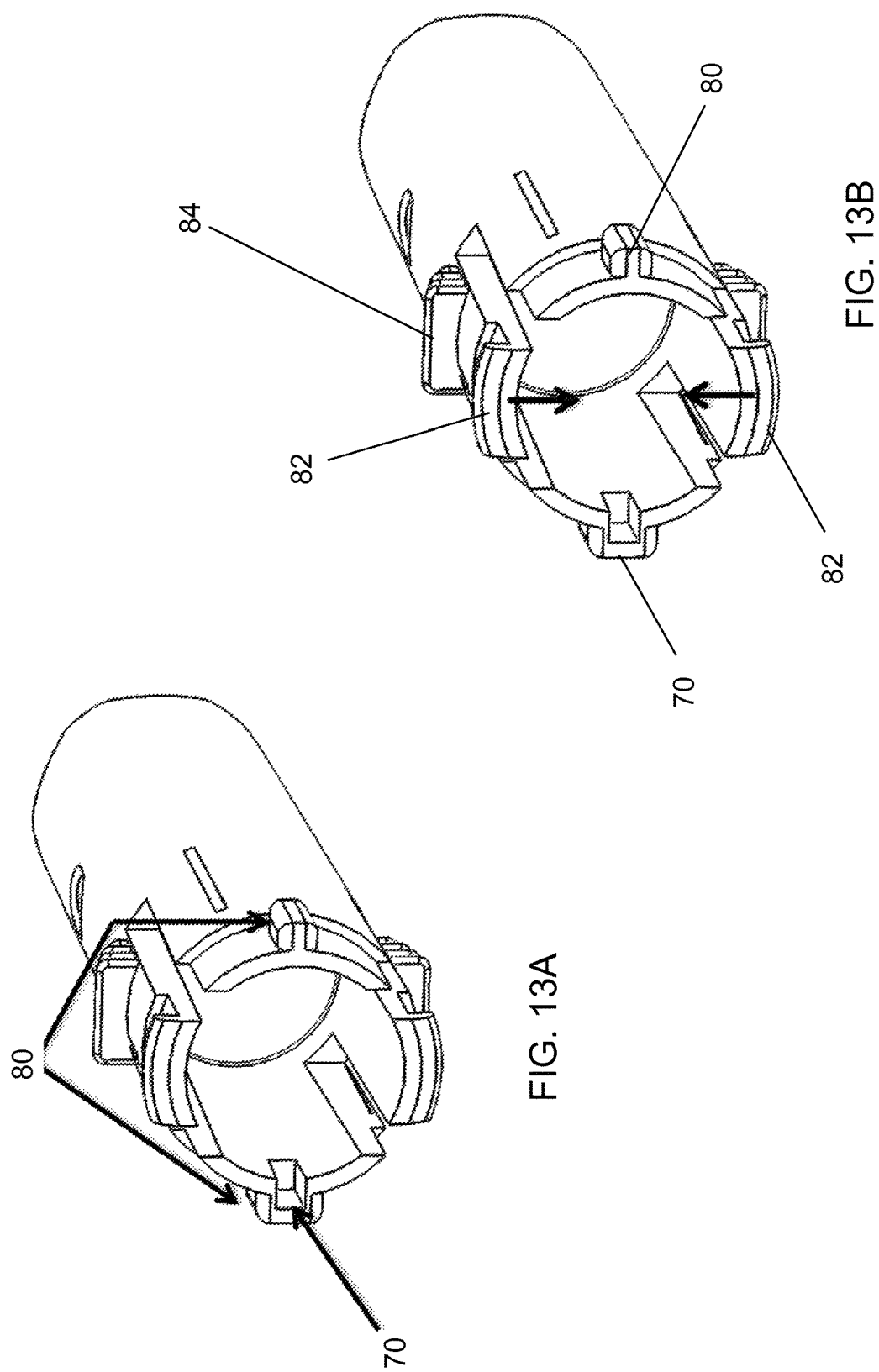

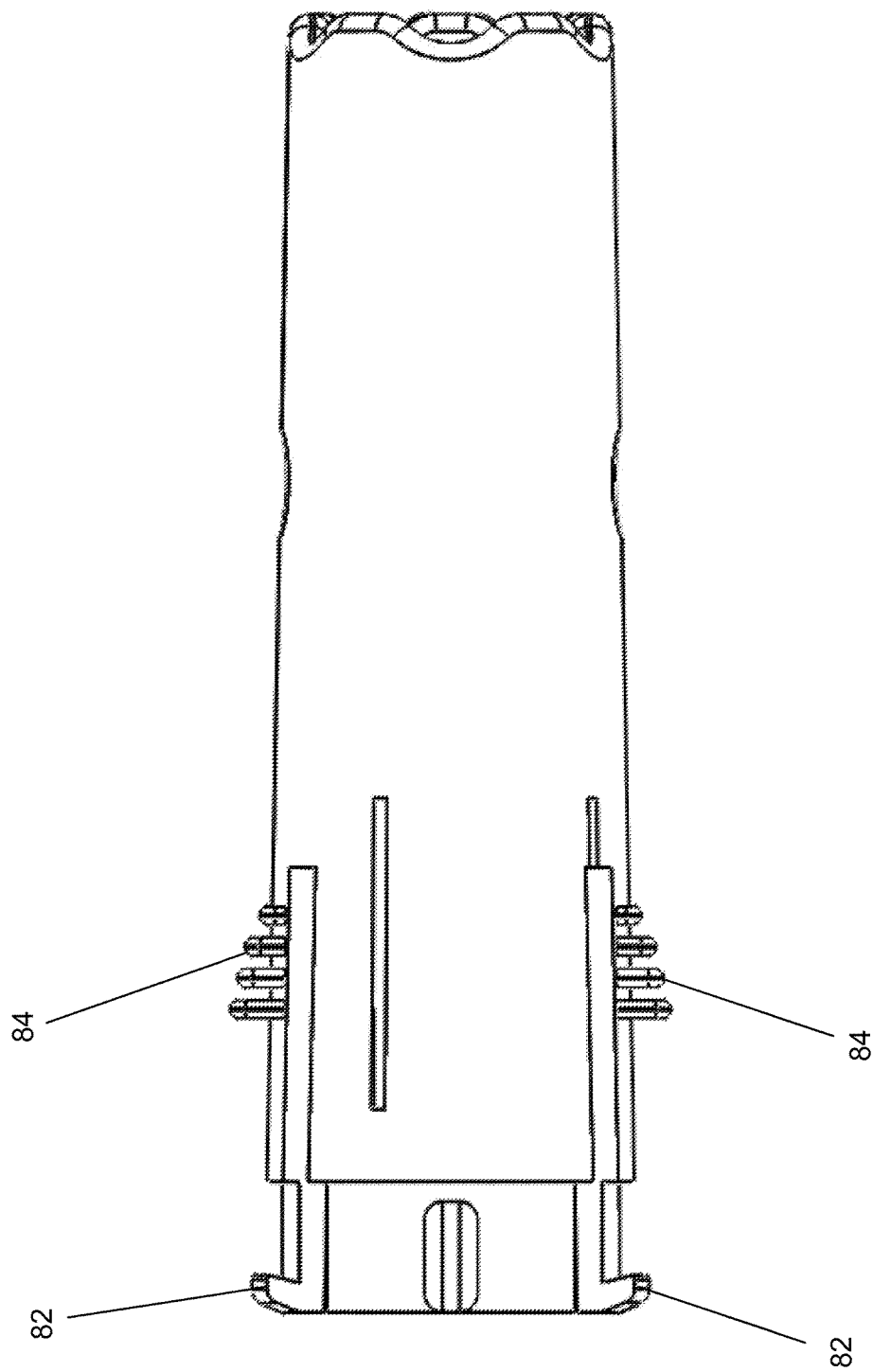

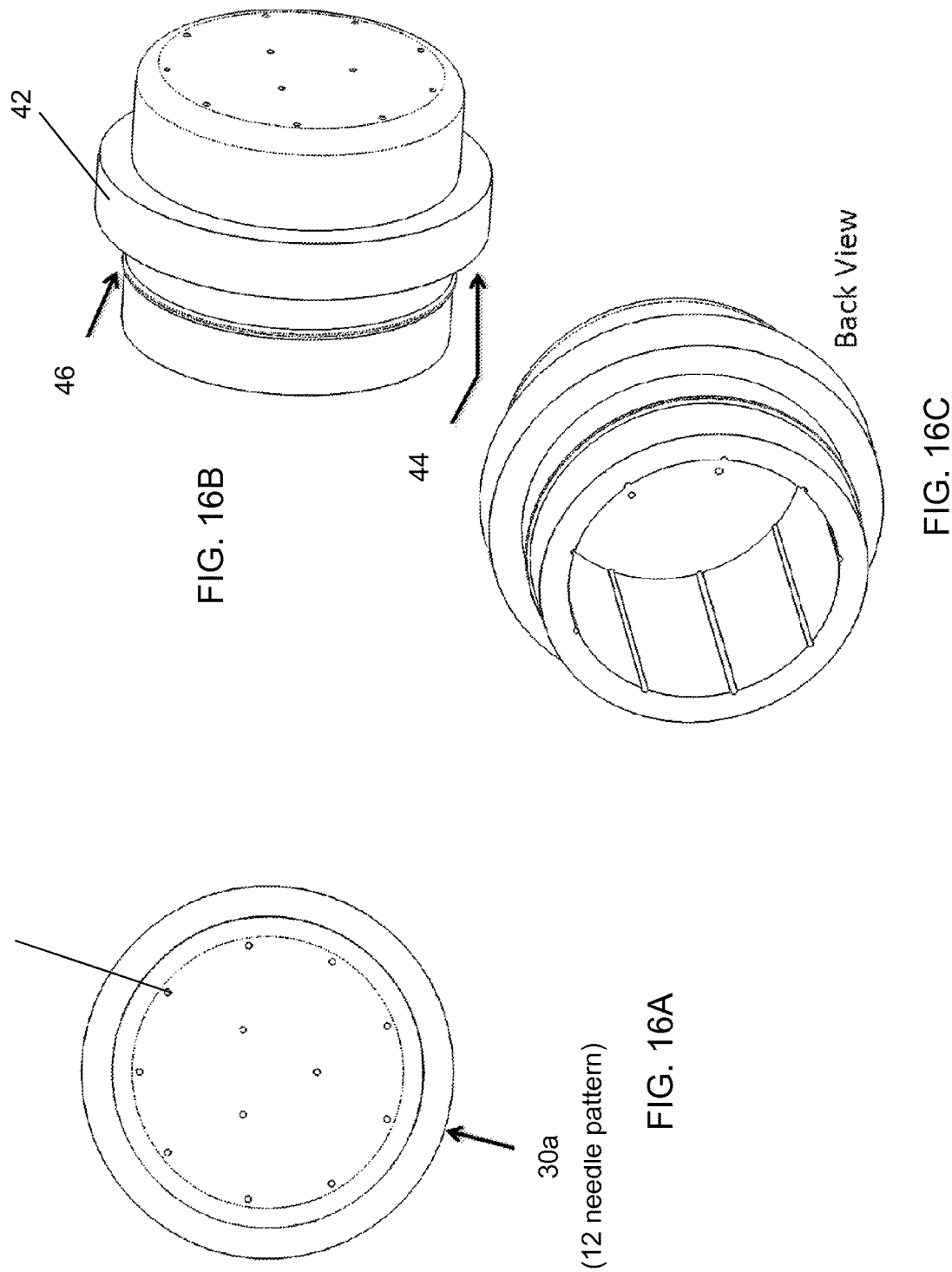

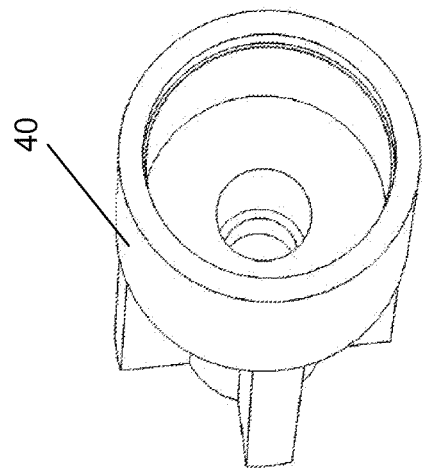
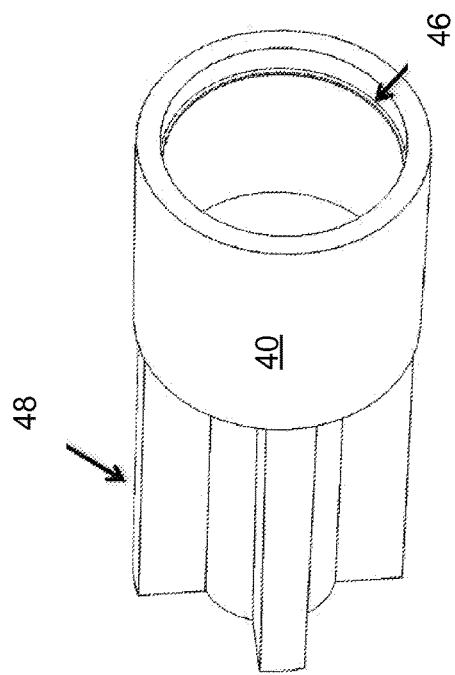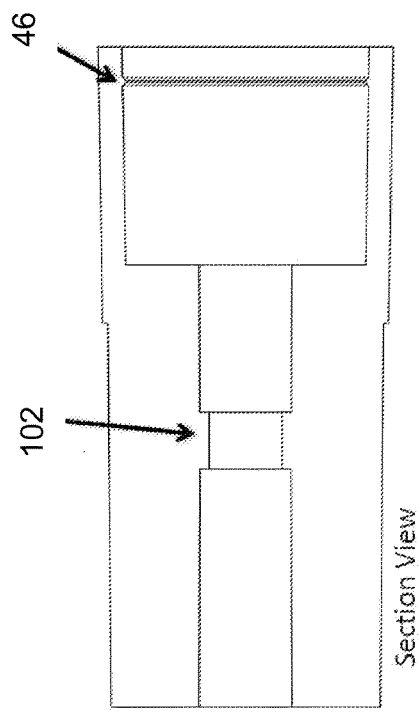

SKIN PUNCTURING DEVICE

This application claims benefit of and priority to U.S. Provisional Application No. 61/911,530, filed Dec. 4, 2013, by Jared Spendlove, et al., and U.S. Provisional Application No. 61/938,720, filed Feb. 14, 2014, by Jared Spendlove, et al., and is entitled to those filing dates for priority in whole or in part. The specifications, figures, appendices, and complete disclosures of U.S. Provisional Application Nos. 61/911,530 and 61/938,720 are incorporated herein by specific reference for all purposes.

FIELD OF INVENTION

This invention relates to a device and apparatus for puncturing skin.

BACKGROUND OF THE INVENTION

A variety of devices for repeatedly puncturing the skin are known in the art, such as disclosed in U.S. Pat. Nos. 6,345,553; 6,505,530; and 8,029,527; and U.S. Pub. Nos. 2005/0010236 and 2012/0123462; all of which are incorporated herein by specific reference in their entireties for all purposes. However, the prior art lacks several health and safety protective features.

SUMMARY OF THE INVENTION

In various exemplary embodiments, the present invention comprises a needle assembly that can be removably attached to a handpiece with a drive mechanism effecting reciprocating movements. Such drive mechanisms include, but are not limited to, "wobble drives." In several embodiments, some or all components of the needle assembly are disposable after use.

The needle assembly generally comprises a needle housing removably attached to a drive shaft guide. The needle housing may be cylindrical in shape, hollow, with an open distal end and proximal end. The drive shaft guide likewise is generally cylindrical in shape, with a distal end and proximal end. The distal end of the drive shaft guide fits into the proximal end of the needle housing.

The interior of the needle assembly comprises one or more needles affixed in a needle head holder. Each needle comprises a needle tip and a needle shaft. The needle shaft extends into and is secured by the needle head holder. The needle tip points towards the open distal end of the needle housing, and extends past and retracts within said open distal end during use of the device.

In several embodiments, a plurality of needles are affixed to the needle head holder, and may be placed in a particular pattern. In some embodiments, eleven needles are used in various geometries to provide a maximum separation between all needles in the range 0.075 inches to 0.125 inches, thereby reducing the stress applied to the skin when the needles try to penetrate. The center geometry can be a triangle, a diamond, or some other geometrical pattern (e.g., square, circle, rectilinear, and the like). In one embodiment, the needles are positioned so that each needle tip is equidistant from adjacent tips, thereby minimizing any potential surface tension created that may hinder the penetration of the needles. Needles may all be the same gage, or different gages. Needles may be all the same length, or varying lengths. Needles also may be moved closer to the outside edge of the needle head holder.

In another embodiment, twelve needles are placed in the pattern shown in a needle head, which is then secured to the needle head holder. The needle head comprises a ridge that serves as a stop for a protective cap that fits over the exterior of the needle head to protect the needle tips. A bump or raised element is used to secure the needle head to the needle head holder, which eliminates the need for an adhesive bond.

In several embodiments, the needle head holder is affixed to a drive shaft. In one embodiment, the distal end of the drive shaft extends into a receiving hole where it is secured or affixed by a chemical or mechanical bond, a solvent bond, some form of adhesive, or the like. In an alternative embodiment, the needle head holder is designed to hold a detachable needle head. The needle head holder may comprise one or more alignment tabs that fit within matching slots or holders or tracks in the housing, and prevent the needle head holder from twisting during operation of the device (i.e., when oscillating). A small gap in a cylindrical cavity in the needle head holder provides an insertion point for the drive shaft, which clicks into place, and thus eliminates the need for an adhesive bond.

In one embodiment, the drive shaft comprises a cylindrical shaft with a distal end and a proximal end. The distal end is affixed to the needle head holder. The drive shaft extends through the drive shaft guide, with the proximal end of the drive shaft approximately co-extensive with the proximal end of the drive shaft guide. The proximal end comprises a cup or indentation to receive the end or coupling from the drive mechanism shaft in the handpiece, when attached. The cup or indentation helps prevent the drive mechanism shaft from wandering while oscillating or reciprocating. In several embodiments, the drive shaft may further comprise one or more supports or extended sides to strengthen the shaft and help prevent the shaft from bending or breaking.

In some embodiments, a conical elastomeric spring is affixed to the drive shaft. The distal end of the elastomeric spring comprises a sleeve that fits tightly to the drive shaft, and may be secured with adhesive. If the drive shaft comprises one or more supports or extended sides, the distal end of the elastomeric spring is affixed to the drive shaft in front of said supports or extended sides, so they do not touch the elastomeric spring or interfere with its functioning. The proximal end of the elastomeric spring is affixed or attached to the outside of the distal end of the drive shaft guide.

In one embodiment, the elastomeric spring is in its rested position when the drive shaft is in a retracted position, and may have no tension or some tension on it. It is stretched when the drive shaft is driven forward and the needle tips extend beyond the distal end of the device. In some embodiments, the elastomeric spring stretches approximately 65% before the tips of the needle extend beyond the distal end of the device, thereby requiring a significant amount of tension before the needle tips are exposed. The tension provided by the elastomeric spring helps the drive shaft return to a retracted position as the drive mechanism shaft oscillates or reciprocates. The elastomeric spring may be a simple conical section, ribbed, or stepped, to control the tensile forces at which the elastomer springs back after being stretched longitudinally. The elastomeric spring also provides a liquid-tight seal, thereby preventing liquids (such as blood) from traveling through the needle apparatus and into the handpiece.

In yet another embodiment, the elastomeric spring is cylindrical in shape. It may be uniform in circumference with two open ends which may be chemically bonded to the respective components of the device. In this configuration, the distal end of the cylindrical spring may attach directly to the needle hold holder, which may have a reduced outer circumference at its distal end to receive the cylindrical spring. In yet another embodiment, a mechanical spring may be used with the drive shaft.

In several embodiments, the distal end of the drive shaft comprises two or more tabs that can press together and reopen. This end may then be inserted into a matching cavity or gap in the needle head holder. The tabs are compressed during insertion, and then open when the tabs enter the cavity or gap. The mechanical spring, if used, may encompass the forward portion of the shaft, and is held into place by a ridge or stop positioned along the middle of the shaft.

In another embodiment, the drive shaft guide comprises an alignment key feature or protrusion that aligns the drive shaft guide with the needle housing. The alignment key feature or protrusion fits within a matching slot on the needle housing. The proximal end of the drive shaft guide also comprises a pair of safety tabs, one of which may be rounded. The rounded safety tab interfaces with the handpiece to provide positive feedback of depth of needles (i.e., extension of needle tips) via detents. Depth is controlled by twisting the needle assembly when it is locked into the handpiece. The alignment key feature helps ensure that the "zero mark" on the needle housing aligns with the rounded safety tab. Visual indicator lines can be seen through spaces on the needle housing to indicate depth of needle penetration.

The safety tabs also prevent re-use of the needle assembly. When the needle assembly is connected to the handpiece, the safety tabs open and the proximal end of the drive shaft is pushed past the tabs by the drive mechanism shaft or piston on the handpiece. Sloped sides on the exterior of the proximal end of the drive shaft help push open the safety tabs on the drive shaft guide. The safety tabs are held open while the needle assembly is attached to the handpiece and in use. In one embodiment, a tab or feature on the handpiece holds the safety tabs open. After use, the needle assembly is removed, and the safety tabs close. The safety tabs prevent the drive shaft from moving back to a resting position. If the user tries to reattach the needle assembly to the handpiece, the safety tabs can no longer open, thereby preventing reinsertion of the needle assembly.

In one embodiment, the distal end of the needle housing has rounded, scalloped edges or rounded edges to provide increase comfort and less friction on the skin. One or more venting hubs or pressure relief holes prevent pressure build-up and suction effects as the needle head holder oscillates inside the needle housing.

In yet another embodiment, the proximal end of the needle assembly comprises a pair of alignment tabs that allow the needle assembly to be connected with the handpiece in only one orientation. The alignment key feature or protrusion discussed above may also serve as one of these alignment tabs. One or more locking tabs may be used to lock the needle assembly in place with the handpiece. The locking tabs may be released by inward pressure on the release points. Depression of the release points allows the needle assembly to engage or disengage from the handpiece. Alternatively, a key feature may be used to lock the needle assembly to the handpiece (i.e., "pen").

In an alternative embodiment, the needle housing comprises a plurality of alignment tracks that receive alignment tabs on the needle head holder, and guide the needle head holder as it oscillates. A drive shaft channel in the proximal end contains the drive shaft as it oscillates. A ridge at the end of the channel provides a stop for the spring surrounding the shaft, as described herein.

In yet a further embodiment, a protective sleeve or sheath is used to cover some or all of the needle assembly. The distal end comprises a small opening that fits around the distal end of the needle housing. The proximal end is open and allows insertion of the needle assembly (or similar device). In one embodiment, the proximal end allows any device approximately 2 inches or less in diameter to be inserted, while the distal end opening is sized to create a water-tight seal around needle assemblies with a diameter of about 0.45 inches or larger. The protective sleeve or sheath is made of material that is elastic and can stretch around objects larger than the openings to ensure a snug, water-tight seal. The material also may be transparent in whole or in part, thereby allowing the inserted device to remain visible. The material also may be tear-resistant and impervious to liquids and fluids.

BRIEF DESCRIPTION OF THE DRAWINGS

FIGS. 8C-H show views of a cylindrical spring attached to a needle head holder.
FIGS. 9A-B show views of a drive shaft guide.
FIGS. 13A-B show views of the proximal end of the needle housing.
FIG. 14 shows a side view of the needle housing.
FIGS. 16A-C show views of a needle head with twelve needles.
FIGS. 17A-C show views of a needle head holder.

DETAILED DESCRIPTION OF EXEMPLARY EMBODIMENTS

Figure 1:
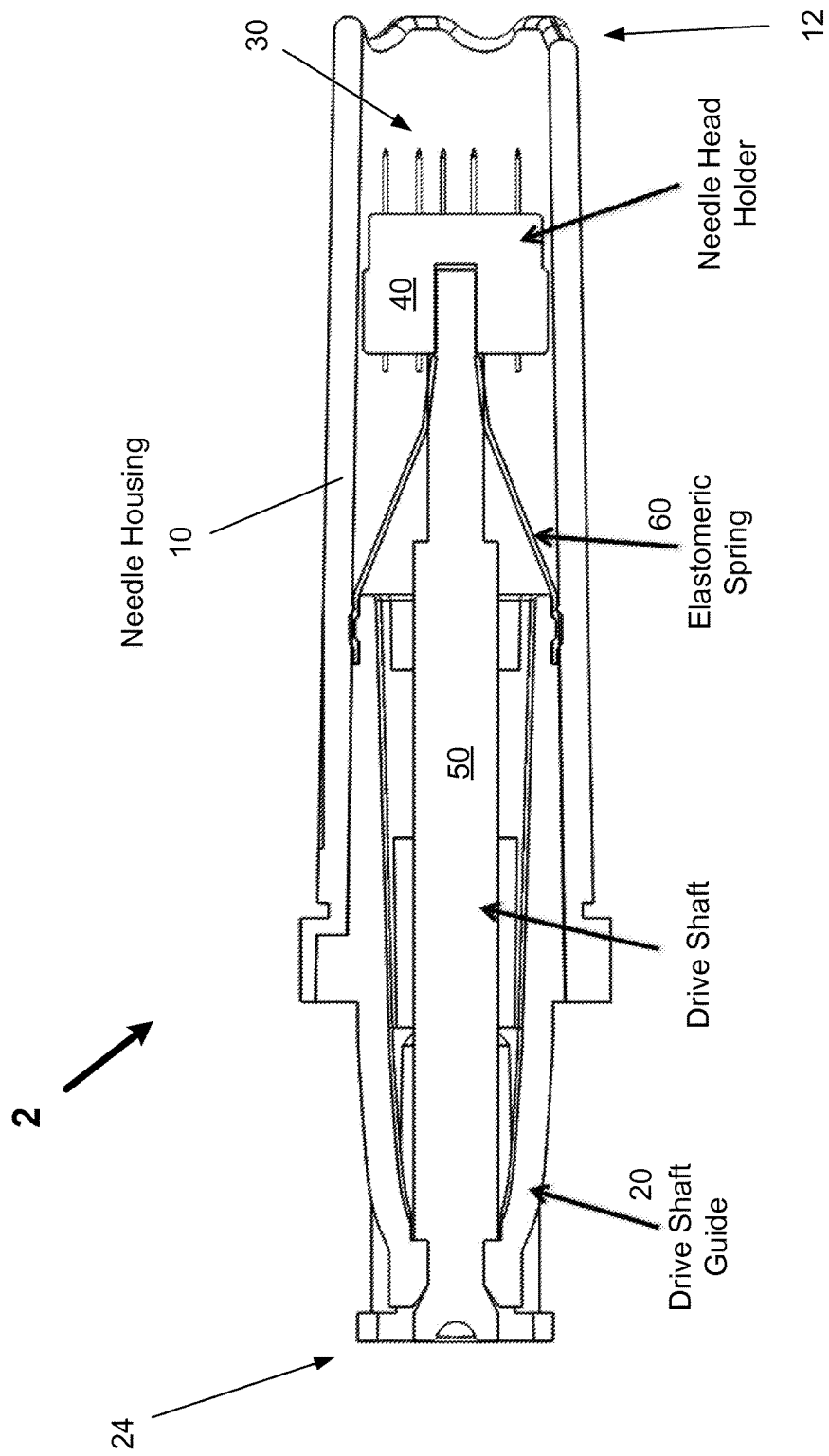
FIG. 1 shows a section view of a device in accordance with an embodiment of the present invention.
Figure 2:
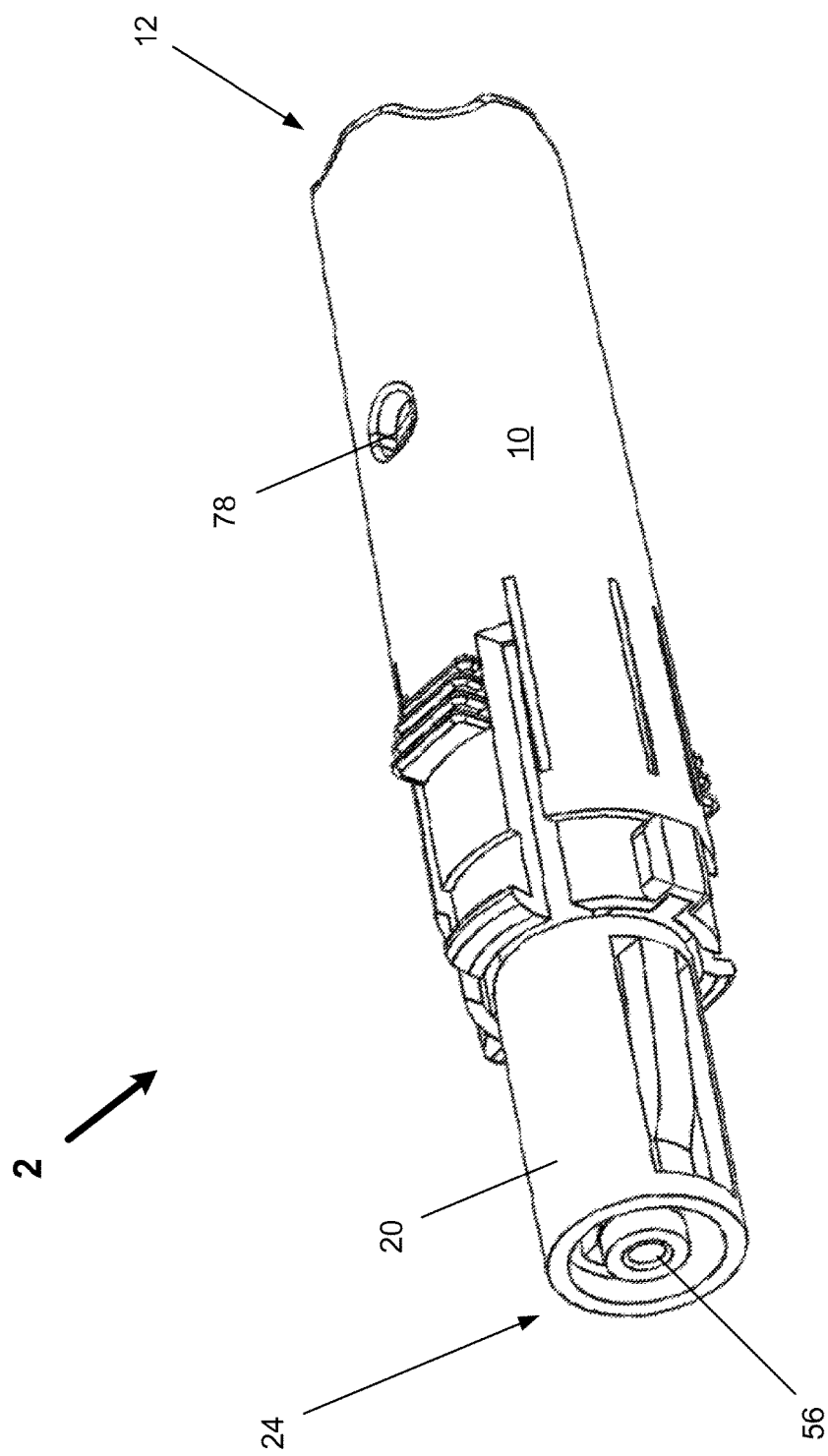
FIG. 2 shows a perspective view of the device of FIG. 1.

As seen in FIGS. 1 and 2, in one exemplary embodiment the present invention comprises a needle assembly 2 that can be removably attached to a handpiece (not shown) with a drive mechanism effecting reciprocating movements. Such drive mechanisms include, but are not limited to, "wobble drives." In several embodiments, some or all components of the needle assembly are disposable after use.

In the embodiment shown, the needle assembly generally comprises a needle housing 10 removably attached to a drive shaft guide 20. The needle housing 10 is cylindrical in shape, hollow, with an open distal end 12 and proximal end 14. The drive shaft guide 20 likewise is generally cylindrical in shape, with a distal end 22 and proximal end 24. The distal end 22 of the drive shaft guide fits into the proximal end 14 of the needle housing 10.

Figure 3B:
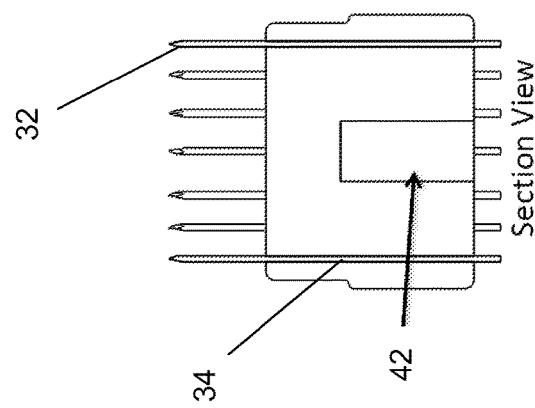
FIGS. 3A-C show views of needles and a needle head holder.

The interior of the needle assembly comprises one or more needles 30 affixed in a needle head holder 40. Each needle comprises a needle tip 32 and a needle shaft 34. The needle shaft 34 extends into and is secured by the needle head holder 40, as seen in FIGS. 3A and 3B. The needle tip 32 points towards the open distal end 12 of the needle housing 10, and extends past and retracts within said open distal end 12 during use of the device.

Figure 4B:
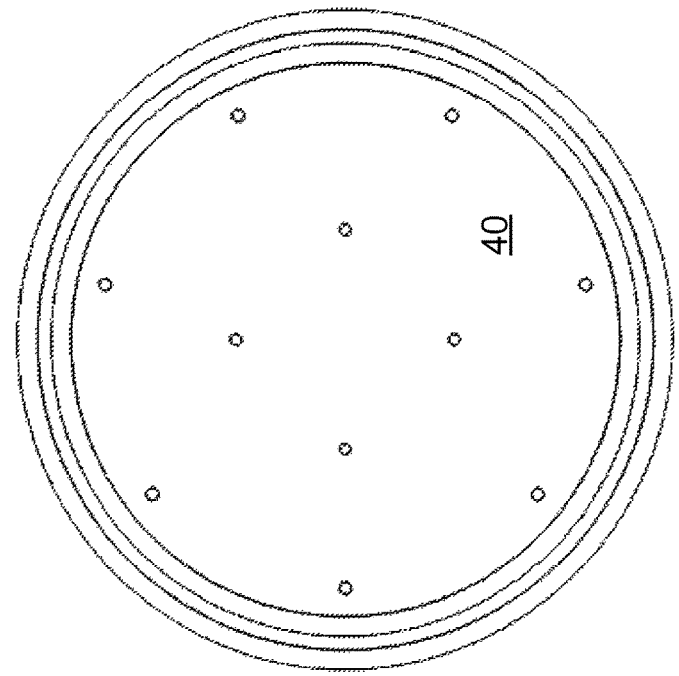
FIGS. 4A-B show views of needle configurations.
Figure 4A:
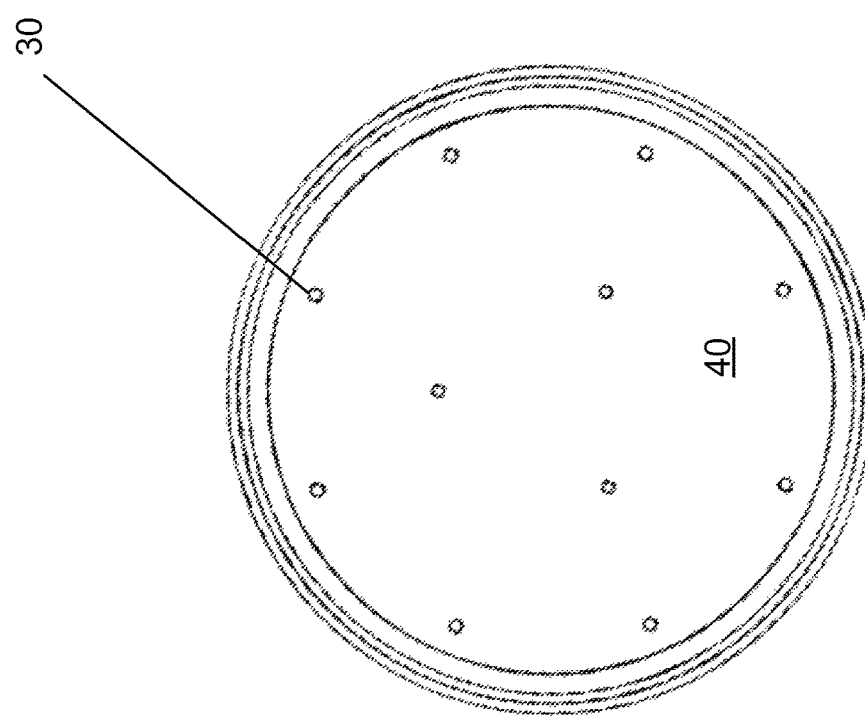

In several embodiments, a plurality of needles 30 are affixed to the needle head holder 40, and may be placed in a particular pattern. In several exemplary embodiments, as shown in FIGS. 4A and 4B, eleven needles are used in various geometries to provide a maximum separation between all needles in the range 0.075 inches to 0.125 inches, thereby reducing the stress applied to the skin when the needles try to penetrate. The center geometry can be a triangle (e.g., FIG. 4A), a diamond (e.g., FIG. 4B), or some other geometrical pattern (e.g., square, circle, rectilinear, and the like). In one embodiment, the needles are positioned so that each needle tip is equidistant from adjacent tips, thereby minimizing any potential surface tension created that may hinder the penetration of the needles. Needles may all be the same gage, or different gages. Needles may be all the same length, or varying lengths. Needles also may be moved closer to the outside edge of the needle head holder.

In another embodiment, as seen in FIGS. 16A-C, twelve needles 30 are placed in the pattern 30a shown in a needle head 42, which is then secured to the needle head holder 40. In one embodiment, the pattern is the optimal packing of 12 points in a circle (i.e., maximizing the minimum pairwise distance among the points spread in a circle centered in the origin). Additional information about the distribution of points in a circle (such as needles on the needle head holder) may be found in Graham, et al., "Dense packings of congruent circles in a circle," Discrete Mathematics 181 (1998), and H. Melissen, "Densest Packing of Eleven Congruent Circles in a Circle," Geom. Dedicata 50 (1994), both of which are incorporated herein by specific reference for all purposes.

The needle head 42 comprises a ridge 44 that serves as a stop for a protective cap that fits over the exterior of the needle head to protect the needle tips. One or more bumps or raised element 46 is used to secure the needle head 42 to the needle head holder 40, which eliminates the need for an adhesive bond. In the embodiment shown in FIG. 20, bumps 46 on the needle head and the needle head holder are forced past each other to create a tight lock, thereby removing the need for an adhesive.

Figure 3C:
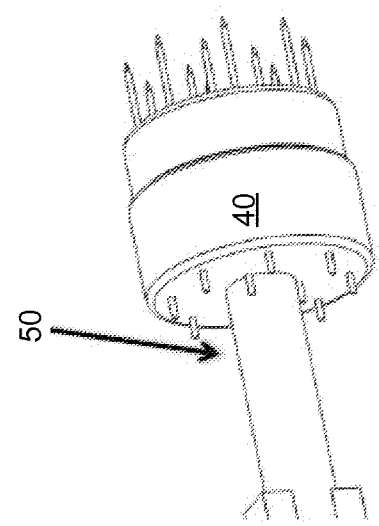
Figure 3A:
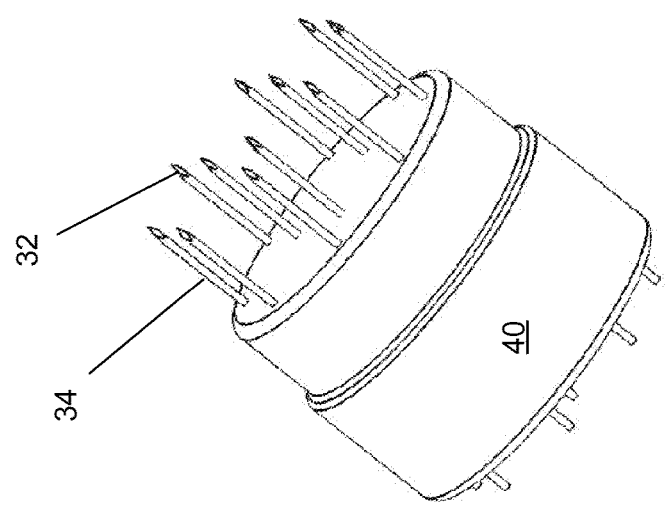

As seen in FIG. 3C, the needle head holder 40 is affixed to a drive shaft 50. As seen in FIG. 3B, the distal end 52 of the drive shaft extends into a receiving hole 42 where it is secured or affixed by a chemical or mechanical bond, a solvent bond, some form of adhesive, or the like.

FIGS. 17A-C shows an alternative embodiment of a needle head holder 40 designed to hold a detachable needle head 42. The needle head holder comprises one or more alignment tabs 48 that fit within matching slots or holders or tracks in the housing, as discussed below, and prevent the needle head holder from twisting during operation of the device (i.e., when oscillating). As seen in the section view in FIG. 17C, a small gap 102 in a cylindrical cavity in the needle head holder provides an insertion point for the drive shaft 50, which clicks into place, and thus eliminates the need for an adhesive bond, as described above.

Figure 5A:
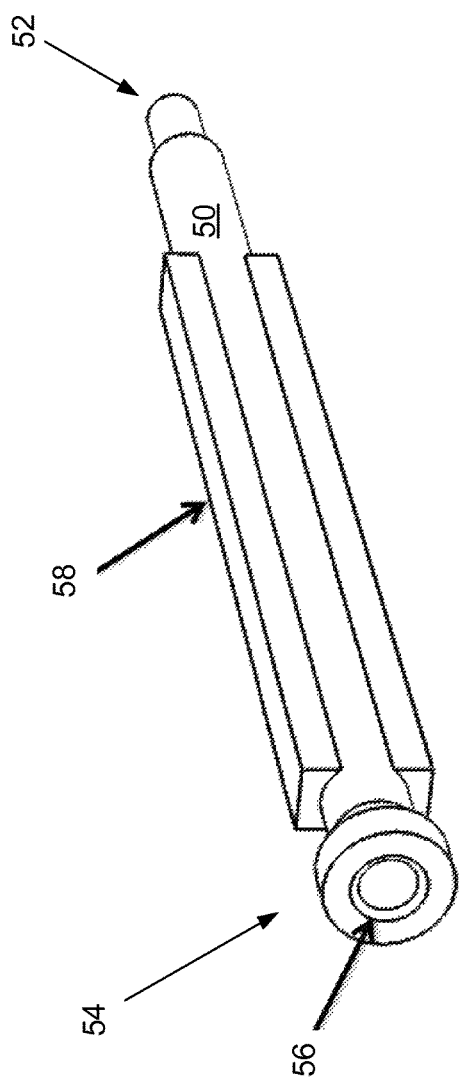
FIGS. 5A-B show views of a drive shaft.
Figure 5B:
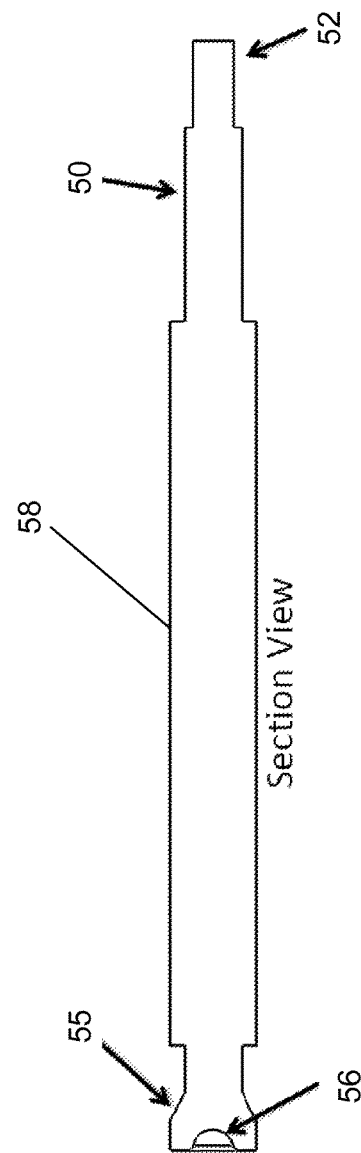

As seen in FIGS. 5A and 5B, in one embodiment the drive shaft 50 comprises a cylindrical shaft with a distal end 52 and a proximal end 54. The distal end 52 is affixed to the needle head holder 40, as described above. The drive shaft extends through the drive shaft guide 20, with the proximal end 54 of the drive shaft 50 approximately co-extensive with the proximal end 24 of the drive shaft guide 20. As seen in FIG. 5A, the proximal end 54 comprises a cup or indentation 56 to receive the end or coupling from the drive mechanism shaft in the handpiece, when attached. The cup or indentation 56 helps prevent the drive mechanism shaft from wandering while oscillating or reciprocating. In several embodiments, the drive shaft 50 may further comprise one or more supports or extended sides 58 to strengthen the shaft and help prevent the shaft from bending or breaking.

Figure 6:
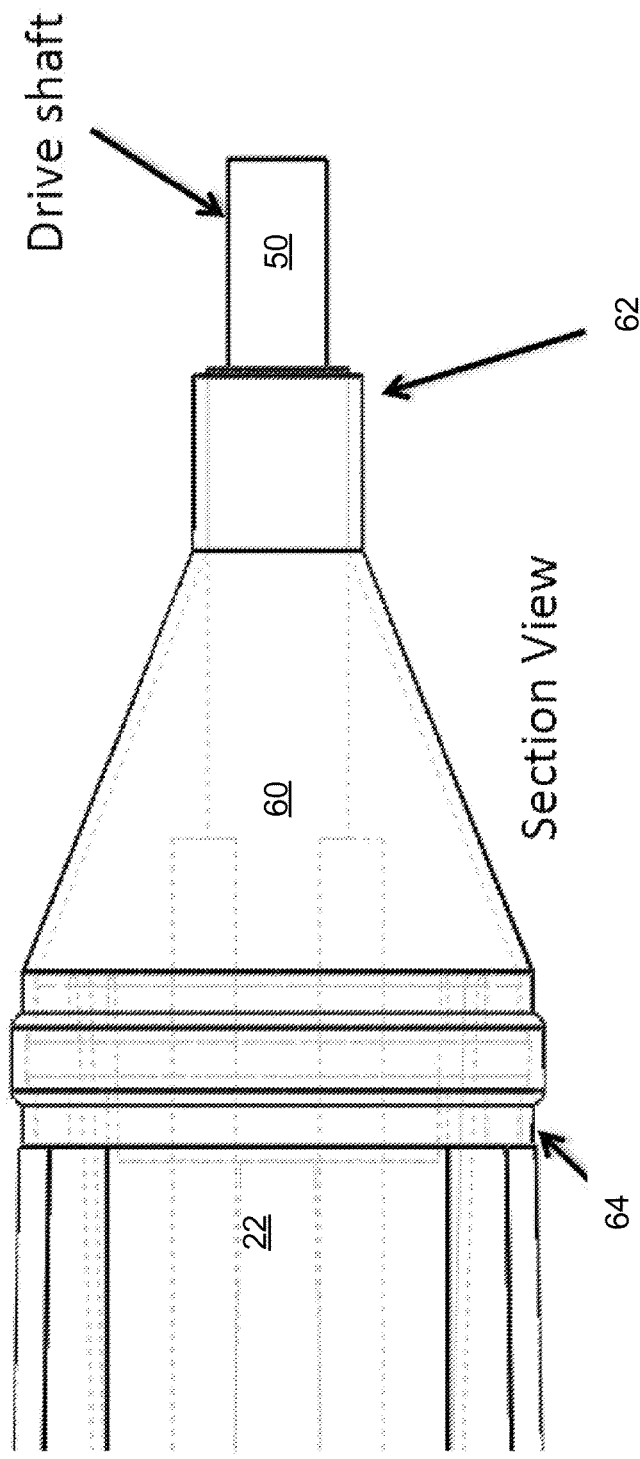
FIG. 6 shows a section view of an elastomeric spring.
Figure 7B:
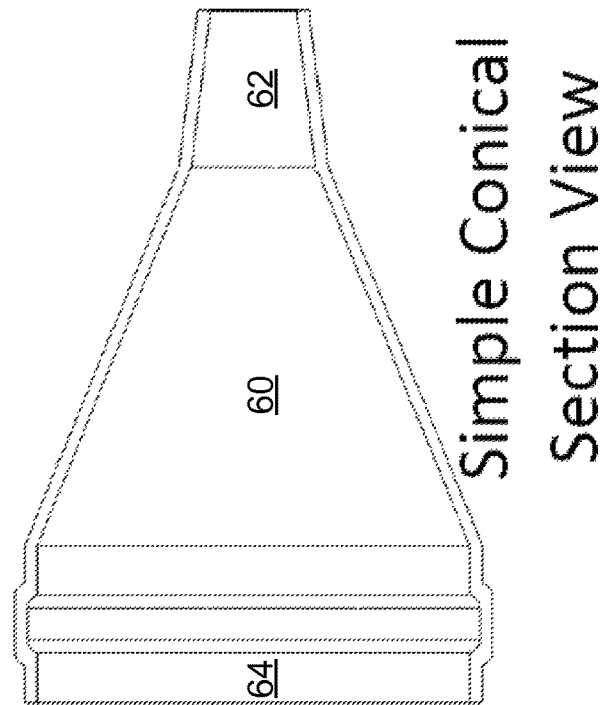
FIGS. 7A-B show views of a conical elastomeric spring.
Figure 7A:
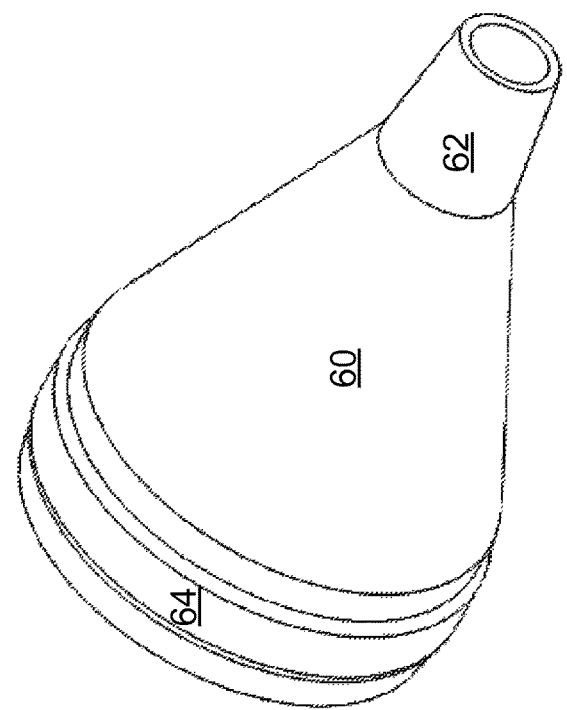

As seen in FIG. 6, a conical elastomeric spring 60 is affixed to the drive shaft 50. The distal end 62 of the elastomeric spring 60 comprises a sleeve that fits tightly to the drive shaft, and may be secured with adhesive. If the drive shaft 50 comprises one or more supports or extended sides 58, as described above, the distal end 62 of the elastomeric spring is affixed to the drive shaft in front of said supports or extended sides, so they do not touch the elastomeric spring or interfere with its functioning. The proximal end 64 of the elastomeric spring is affixed or attached to the outside of the distal end 22 of the drive shaft guide.

In one embodiment, the elastomeric spring is in its rested position when the drive shaft is in a retracted position, and may have no tension or some tension on it. It is stretched when the drive shaft is driven forward and the needle tips extend beyond the distal end of the device. In one embodiment, the elastomeric spring stretches approximately 65% before the tips of the needle extend beyond the distal end of the device, thereby requiring a significant amount of tension before the needle tips are exposed. The tension provided by the elastomeric spring helps the drive shaft return to a retracted position as the drive mechanism shaft oscillates or reciprocates. The elastomeric spring may be a simple conical section, ribbed, or stepped, as seen in FIGS. 7A-B and 8A-B, to control the tensile forces at which the elastomer springs back after being stretched longitudinally. The elastomeric spring also provides a liquid-tight seal, thereby preventing liquids (such as blood) from traveling through the needle apparatus and into the handpiece.

Figure 8B:
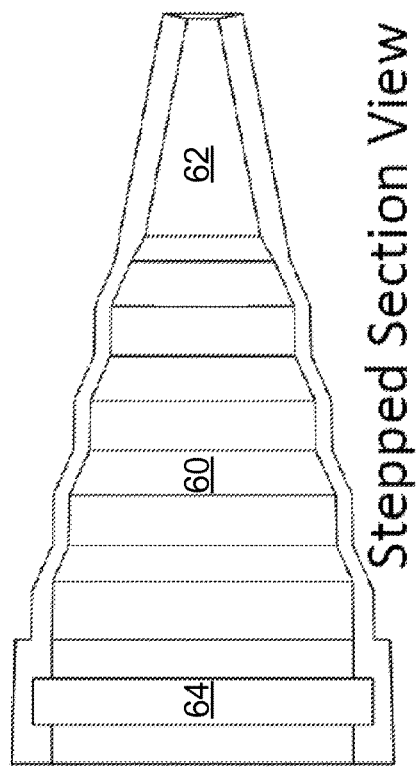
FIGS. 8A-B show views of a ribbed elastomeric spring and a stepped elastomeric spring.
Figure 8A:
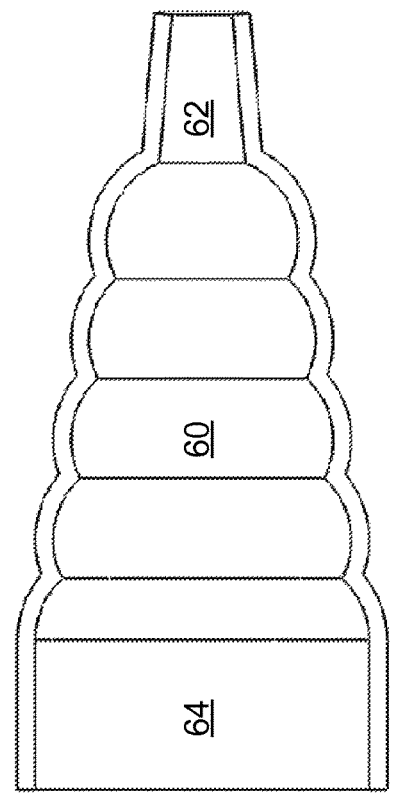
Figure 8F:
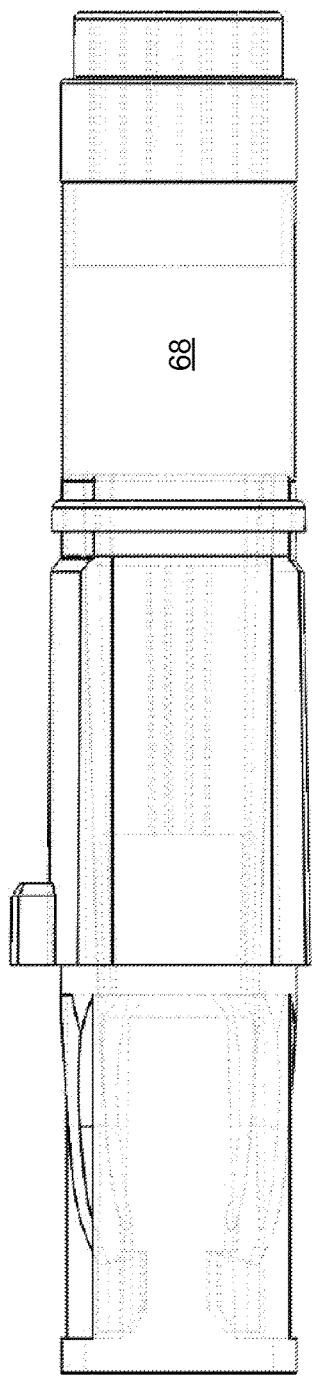
Figure 8G:
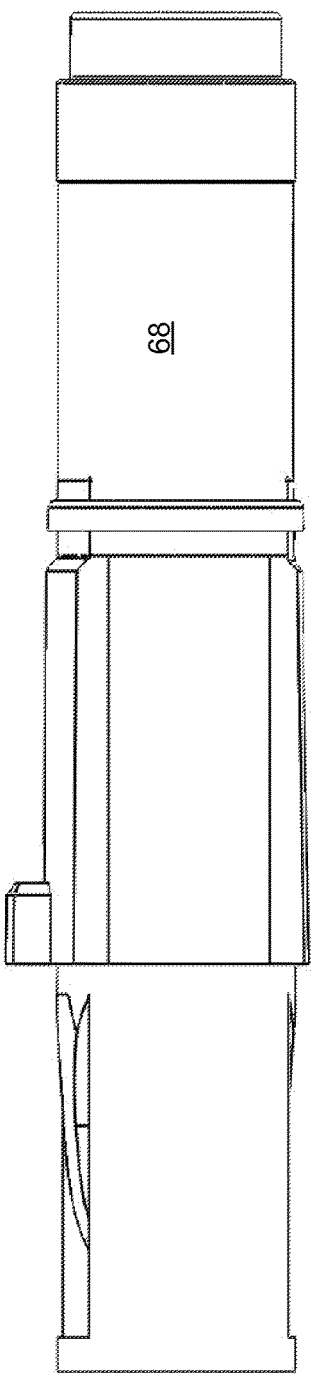
Figure 8H:
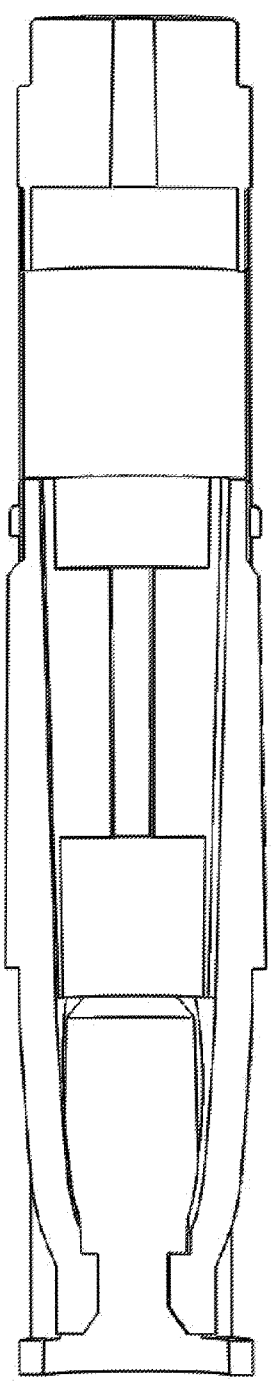
Figure 10B:
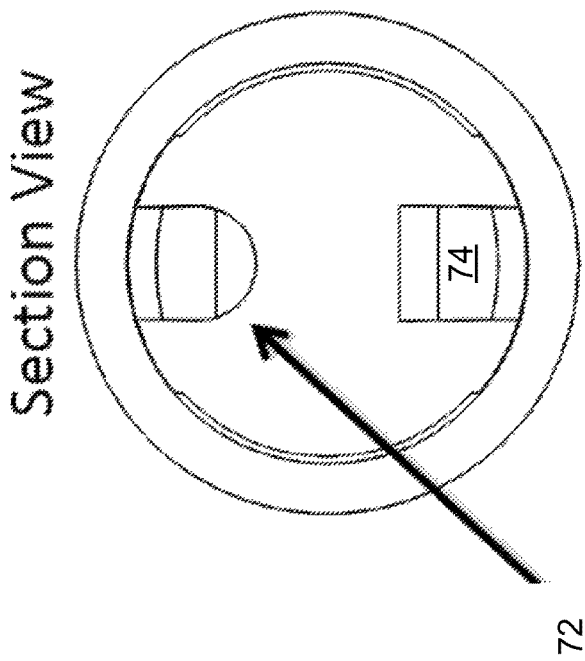
FIGS. 10A-B show views of the proximal end of the device of FIG. 1 with safety tabs.
Figure 10A:
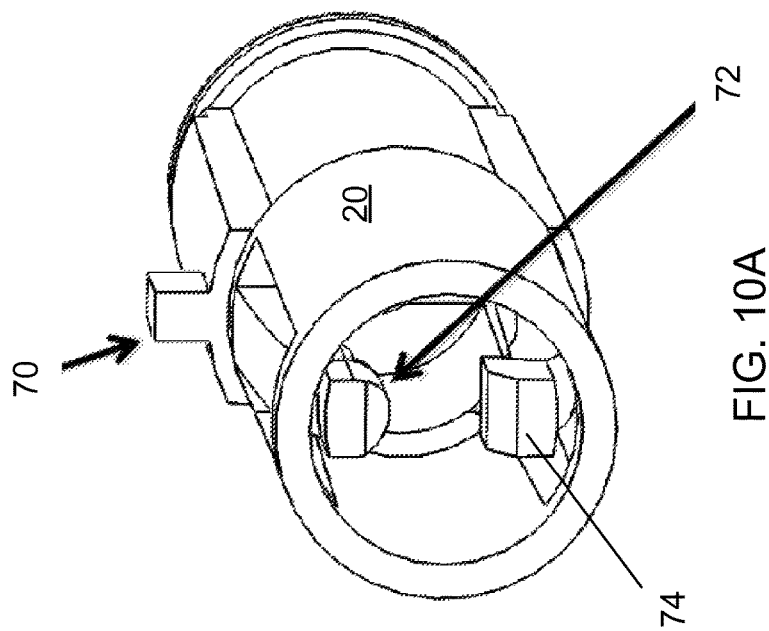

In yet another embodiment, as seen in FIGS. 8C-E, the elastomeric spring 68 is cylindrical in shape. In the embodiment shown, it is uniform in circumference with two open ends which may be chemically bonded to the respective components of the device. In this configuration, the distal end of the cylindrical spring may attach directly to the needle hold holder 40, which may have a reduced outer circumference 69 at its distal end to receive the cylindrical spring. Side and cross-sectional views of an alternative form are shown in FIGS. 8F-H.

Figure 18A:
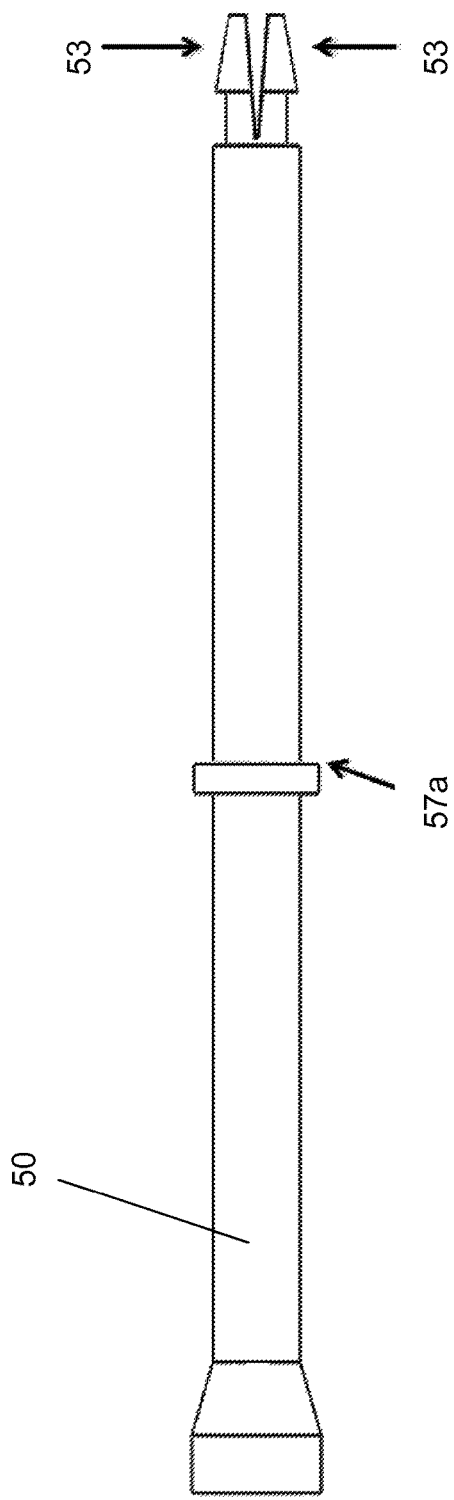
FIGS. 18A-B show views of a drive shaft.
Figure 18B:
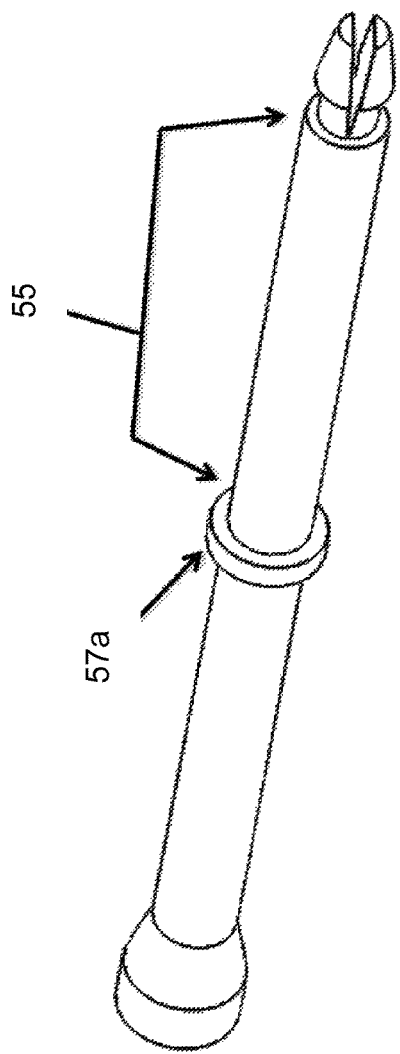
Figure 20:
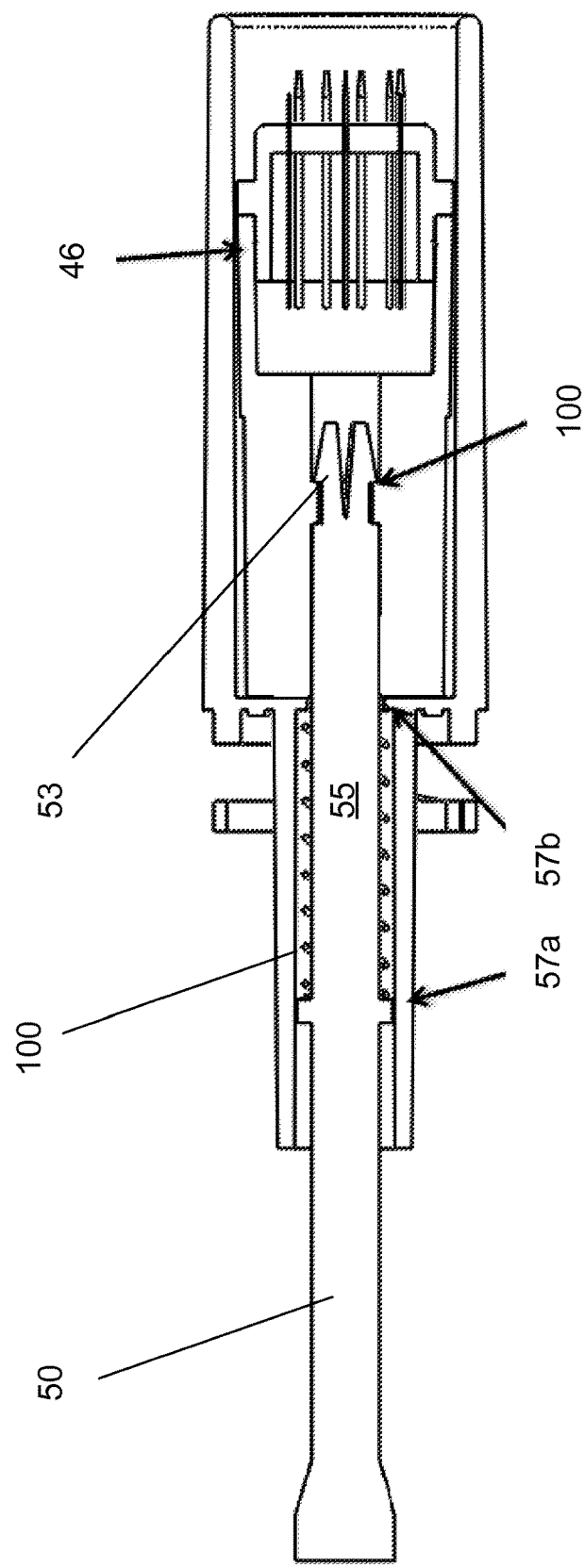
FIG. 20 shows a cutaway view of a needle assembly.

In yet another embodiment, as seen in FIG. 20, a mechanical spring 100 may be used with the drive shaft 50. In the embodiment shown in FIGS. 18A-B and 20, the distal end 52 of the drive shaft comprise two or more tabs 53 that can press together and reopen. This end may then be inserted into a matching cavity or gap 102 in the needle head holder, as seen in FIGS. 17C and 20. The tabs are compressed during insertion, and then open when the tabs enter the cavity or gap (i.e., the shaft is inserted and clicks into place), thereby removing the need for an adhesive or similar attachment means. The spring may encompass the forward portion 55 of the shaft, and is held into place by a ridge or stop 57a positioned along the middle of the shaft 50, and a similar ridge or protrusion 57b extending from the inside of the housing around the opening through which shaft is inserted.

Figure 12:
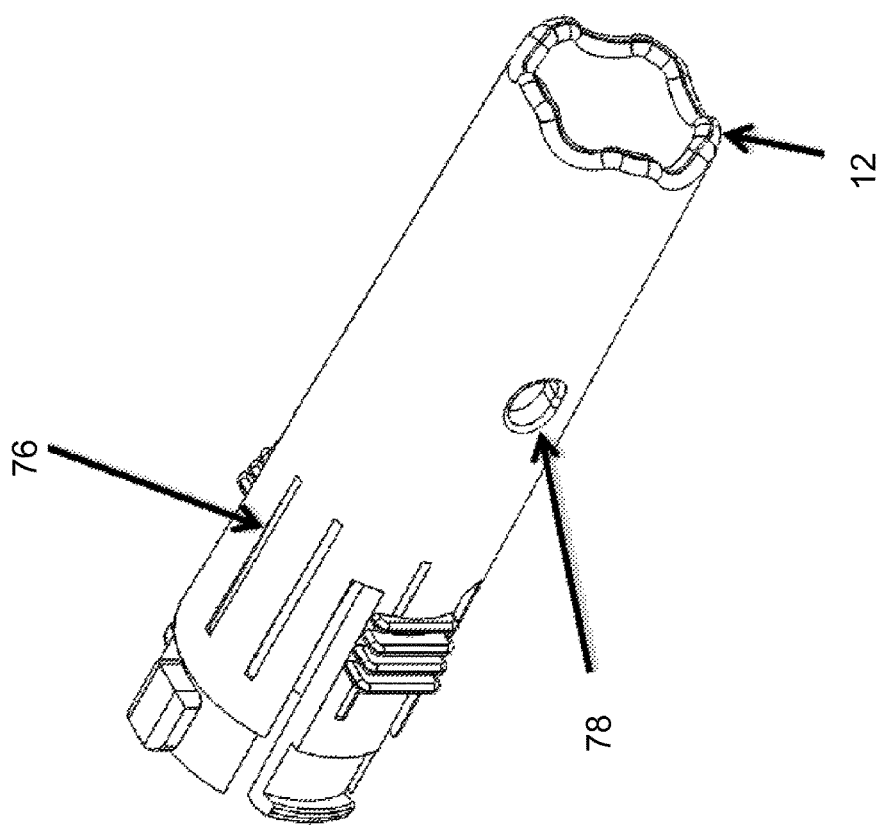
FIG. 12 shows a perspective view of a needle housing.
Figure 15C:
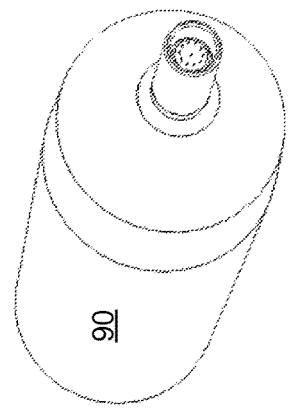
FIGS. 15A-E show views of a protective sleeve or sheath.
Figure 15D:
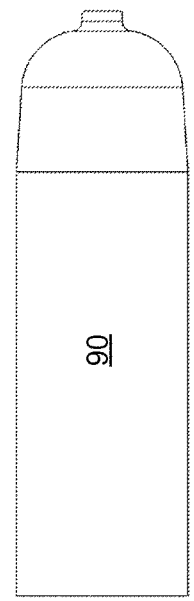
Figure 15E:
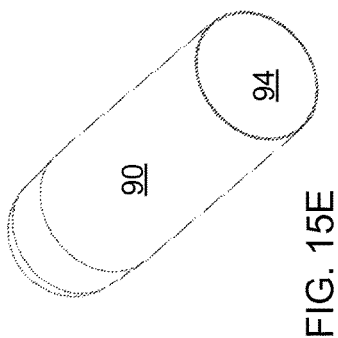
Figure 15A:
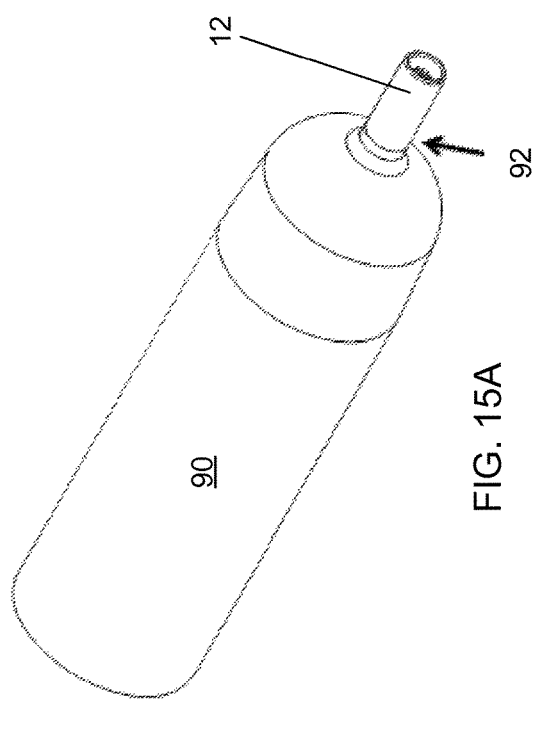
Figure 15B:
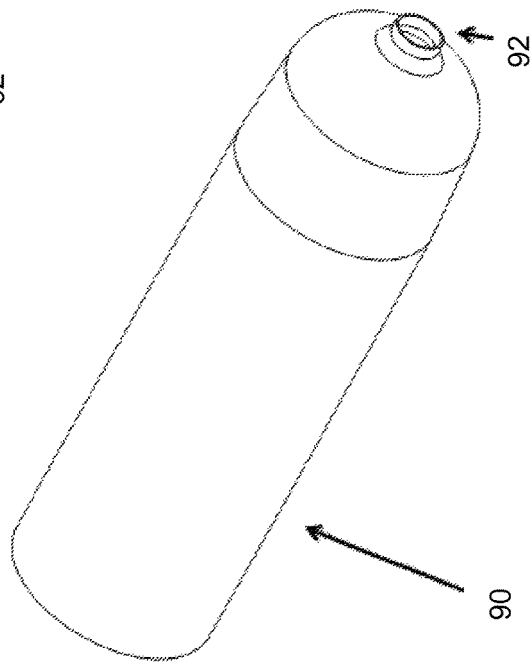

In another embodiment, as seen in FIGS. 9A-B and 10A-B, the drive shaft guide comprises an alignment key feature or protrusion 70 that aligns the drive shaft guide with the needle housing. The alignment key feature or protrusion 70 fits within a matching slot on the needle housing. The proximal end of the drive shaft guide also comprises a pair of safety tabs 72, 74, one of which may be rounded 72. The rounded safety tab interfaces with the handpiece to provide positive feedback of depth of needles (i.e., extension of needle tips) via detents. Depth is controlled by twisting the needle assembly when it is locked into the handpiece. The alignment key feature helps ensure that the "zero mark" on the needle housing aligns with the rounded safety tab 72. Visual indicator lines 76 can be seen through spaces on the needle housing to indicate depth of needle penetration, as shown in FIG. 12.

Figure 11A:
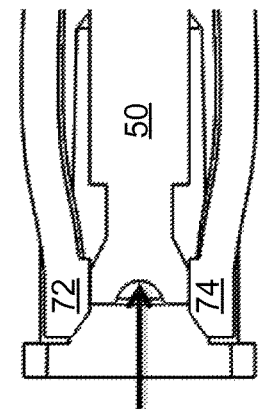
FIGS. 11A-E show sectional views of the interaction of the drive shaft with the safety tabs.
Figure 11B:
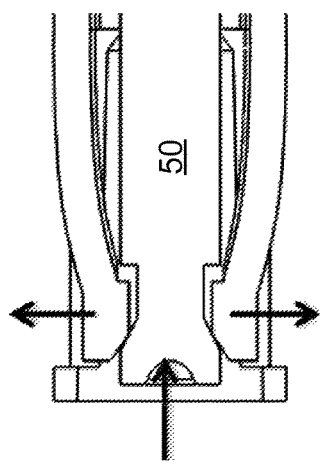
Figure 11C:
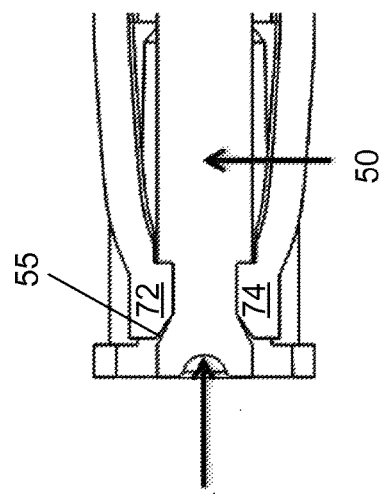
Figure 11E:
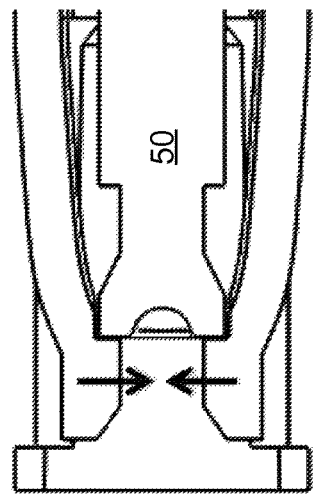
Figure 11D:
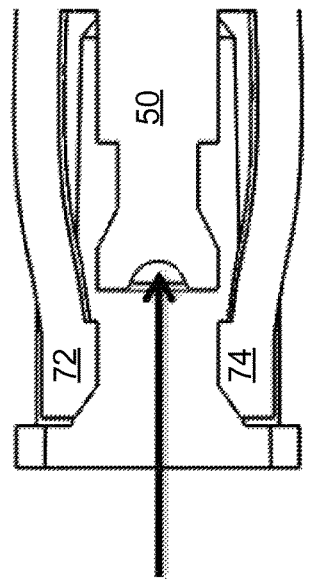

The safety tabs 72, 74 also prevent re-use of the needle assembly. As seen in FIGS. 11A-D, when the needle assembly is connected to the handpiece, the safety tabs open and the proximal end 54 of the drive shaft 50 is pushed past the tabs by the drive mechanism shaft or piston on the handpiece. Sloped sides 55 on the exterior of the proximal end of the drive shaft help push open the safety tabs on the drive shaft guide. The safety tabs are held open while the needle assembly is attached to the handpiece and in use. In one embodiment, a tab or feature on the handpiece holds the safety tabs open. After use, the needle assembly is removed, and the safety tabs close, as seen in FIG. 11E. The safety tabs prevent the drive shaft from moving back to a resting position. If the user tries to reattach the needle assembly to the handpiece, the safety tabs can no longer open, and prevent reinsertion of the needle assembly.

Figure 19C:
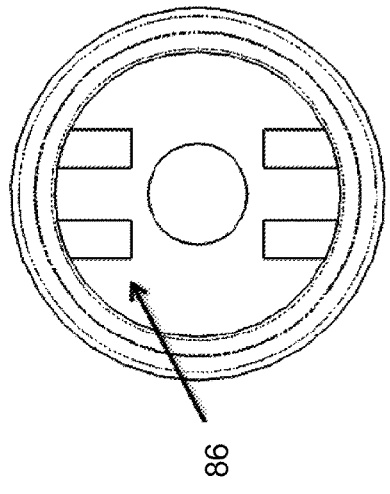
FIGS. 19A-C show views of a needle housing.
Figure 19A:
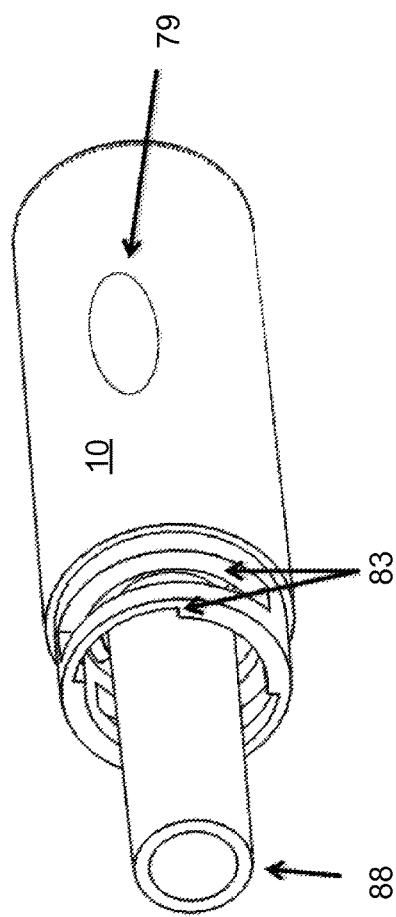
Figure 19B:
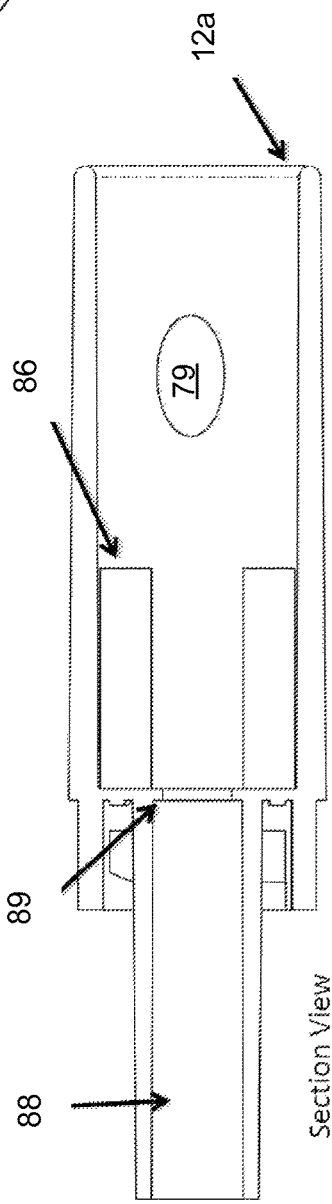

In one embodiment, the distal end 12 of the needle housing has rounded, scalloped edges or rounded edges to provide increase comfort and less friction on the skin. A rounded front end or edge 12a, as seen in FIG. 19B, provides a smooth surface that is in contact with the skin. One or more venting hubs 78 or pressure relief holes 79 prevent pressure build-up and suction effects as the needle head holder 40 oscillates inside the needle housing.

In yet another embodiment, as seen in FIGS. 13A-B and 14, the proximal end of the needle assembly comprises a pair of alignment tabs 80 that allow the needle assembly to be connected with the handpiece in only one orientation. The alignment key feature or protrusion 70 discussed above may also serve as one of these alignment tabs 80. One or more locking tabs 82 may be used to lock the needle assembly in place with the handpiece. The locking tabs 82 may be released by inward pressure on the release points 84. Depression of the release points allows the needle assembly to engage or disengage from the handpiece. Alternatively, a key feature 83 may be used to lock the needle assembly to the handpiece (i.e., "pen"), as seen in FIG. 19A.

In the embodiment shown in FIGS. 19A-C and 20, the needle housing 10 comprises a plurality of alignment tracks 86 that receive alignment tabs 48 on the needle head holder, and guide the needle head holder as it oscillates. A drive shaft channel 88 in the proximal end contains the drive shaft as it oscillates. A ridge 89 at the end of the channel provides a stop for the spring surrounding the shaft, as described herein. FIG. 20 shows a completed needle assembly for this embodiment.

In yet a further embodiment, as seen in FIGS. 15A-E, a protective sleeve or sheath 90 is used to cover some or all of the needle assembly. The distal end comprises a small opening 92 that fits around the distal end of the needle housing 12. The proximal end is open 94 and allows insertion of the needle assembly (or similar device). In one embodiment, the proximal end allows any device approximately 2 inches or less in diameter to be inserted, while the distal end opening 92 is sized to create a water-tight seal around needle assemblies with a diameter of about 0.45 inches or larger. The protective sleeve or sheath is made of material that is elastic and can stretch around objects larger than the openings to ensure a snug, water-tight seal. The material also may be transparent in whole or in part, thereby allowing the inserted device to remain visible. The material also may be tear-resistant and impervious to liquids and fluids.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A device for skin puncturing, comprising:
   a housing with a proximal end and a distal end and an interior and an exterior, said distal end comprising an opening;
   a reciprocating drive shaft with a proximal end and a distal end disposed within said housing;
   a needle head directly or indirectly attached to the distal end of the reciprocating drive shaft;
   a plurality of needles extending from the needle head, each needle comprising a needle tip, wherein the needle tips periodically extend beyond the opening in the distal end of the housing with motion of the reciprocating drive shaft; and
   one or more safety tabs adapted to open when the device is mounted on a handpiece, and adapted to permanently close when the device is removed from said handpiece, and thereby prevent the device from being remounted on said handpiece.

2. The device of claim 1, wherein there are 11 or 12 needles extending from the needle head.

3. The device of claim 1, wherein the needles are placed so that the maximum separation between adjacent needles is in the range of 0.075 inches to 0.125 inches.

4. The device of claim 1, wherein the needles are placed so that each needle tip is equidistant from adjacent needle tips.

5. The device of claim 1, further comprising a spring affixed to the reciprocating drive shaft.

6. The device of claim 5, wherein the spring is in a state of tension when the reciprocating drive shaft has moved to a position such that said needle tips extend beyond the opening in the distal end of the housing, such that the tension helps retraction of the reciprocating drive shaft.

7. The device of claim 5, wherein said spring is an elastomeric spring.

8. The device of claim 5, wherein said spring is a mechanical spring.

9. The device of claim 1, further comprising a drive shaft guide affixed to the interior of said housing, said drive shaft guide adapted to receive and guide the reciprocating drive shaft while in motion.

10. The device of claim 9, said drive shaft guide further comprising at least one alignment key feature adapted to fit with a matching slot on the needle housing.

11. The device of claim 9, said drive shaft guide further comprising a depth tab to indicate the distance the needle tips extend beyond the opening in the distal end of the housing with full extension of the reciprocating drive shaft.

12. The device of claim 1, wherein the opening in the distal end of the housing comprises round or scalloped edges, or a combinations thereof.

13. The device of claim 1, further comprising a protective sleeve adapted to cover some or all of the exterior of the housing, said protective sleeve comprising a proximal end with a large opening and a distal end with a small opening, said small opening adapted to fit securely around the distal end of the housing.

14. The device of claim 13, wherein said protective sleeve is elastic and water-proof.

15. The device of claim 13, wherein said protective sleeve is transparent in whole or in part.

16. A device for skin puncturing, comprising:
a housing with a proximal end and a distal end and an interior and an exterior, said distal end comprising an opening;
a reciprocating drive shaft with a proximal end and a distal end disposed within said housing;
a needle head directly or indirectly attached to the distal end of the reciprocating drive shaft;
a plurality of needles extending from the needle head, each needle comprising a needle tip, wherein the needle tips periodically extend beyond the opening in the distal end of the housing with motion of the reciprocating drive shaft; and
an elastomeric spring affixed to the reciprocating drive shaft;
further wherein the elastomeric spring provides a liquid-tight seal preventing liquids from traveling through the device.

17. The device of claim 16, wherein the elastomeric spring is conical or cylindrical in shape.

* * * * *